United States Patent [19]

Ziegler et al.

[11] Patent Number: 4,783,464

[45] Date of Patent: Nov. 8, 1988

[54] N-SUBSTITUTED ERGOLINE- AND 9,10-DIDEHYDRO-ERGOLINE-8-CARBOXAMIDE-AND-8-AMINOMETHYL-DERIVATIVES, THEIR PRODUCTION AND THEIR PHARMACEUTICAL COMPOSITION

[75] Inventors: René Ziegler, Basle, Switzerland; Peter Stütz, Vienna, Austria

[73] Assignee: Sandoz Ltd., Basle, Switzerland

[21] Appl. No.: 123,016

[22] Filed: Nov. 19, 1987

Related U.S. Application Data

[63] Continuation of Ser. No. 438,449, Nov. 12, 1982, abandoned.

[30] Foreign Application Priority Data

Nov. 4, 1981 [CH] Switzerland ..................... 7056/81

[51] Int. Cl.$^4$ ................. A61K 31/495; C07D 457/02; C07D 457/06
[52] U.S. Cl. .................................... 514/253; 544/405
[58] Field of Search ........................ 544/405; 514/253

[56] References Cited

U.S. PATENT DOCUMENTS 4,123,613 10/1978 Bernardi et al. .................... 544/408
4,675,404 1/1987 Bernardi et al. .................... 544/238

Primary Examiner—Donald G. Daus
Assistant Examiner—William A. Teoli, Jr.
Attorney, Agent, or Firm—Gerald D. Sharkin; Robert S. Honor; Thomas O. McGovern

[57] ABSTRACT

Novel N-substituted ergoline- and 9,10-didehydro-8-carboxamide- and -8-aminomethyl-derivatives for the treatment of vascular headaches, especially migraine, and of orthostatic hypotension.

26 Claims, No Drawings

N-SUBSTITUTED ERGOLINE- AND 9,10-DIDEHYDRO-ERGOLINE-8-CARBOXAMIDE- AND-8-AMINOMETHYL-DERIVATIVES, THEIR PRODUCTION AND THEIR PHARMACEUTICAL COMPOSITION

This is a continuation of application Ser. No. 438,449, filed Nov. 2, 1982 now abandoned.

The invention relates to novel N-substituted ergoline- and 9,10-didehydro-ergoline-8-carboxamide- and -8-aminomethyl-derivatives, their production and their pharmaceutical compositions.

The present invention provides compounds of formula I

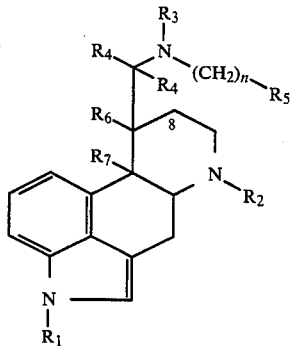

wherein
$R_1$ is $(C_{1-4})$alkyl, or H or a precursor thereof,
$R_2$ is H or $(C_{1-6})$alkyl
$R_3$ is H or $(C_{1-4})$alkyl
the two
$R_4$'s both are H or together are an oxo group
$R_5$ is the radical

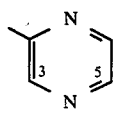

which is unsubstituted or substituted with one or two halogen atoms, $(C_{1-4})$alkyl or -alkoxy groups or with one hydroxy group in position 3 or 5 or, is the radical

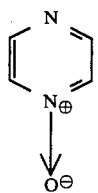

which is unsubstituted or substituted by one or two halogen atoms
$R_6$ and $R_7$ both are H or together are a bond and n is 0, 1 or 2,
hereinafter referred to as compounds of the invention.

The configuration of the side chain in position 8 is either α or β.

As precursors in position 1 are meant such substituents which under physiological conditions may be converted into H. Such substituents are e.g. —CH$_2$OH or $(C_{1-4})$alkoxymethyl, especially CH$_3$OCH$_2$—. Halogen atoms are F, Cl, Br or I, preferably Cl or Br, especially Cl.

Preferred substituents in the compounds of formula I are individually:
$R_1$=H, $(C_{1-4})$alkyl or $(C_{1-4})$alkoxymethyl, especially H, methyl or methoxymethyl, particularly H;
$R_2$=$(C_{1-4})$alkyl, especially methyl or ethyl, particularly methyl;
$R_3$=H or methyl, particularly H; both $R_4$ are together=oxo; $R_5$=unsubstituted 2-pyrazinyl, 4-oxido-2-pyrazinyl or 1H-2-oxo-pyrazin-3-yl, especially unsubstituted 2-pyrazinyl; n=0 or 1, especially 0; $R_6$ and $R_7$ each are H; the configuration of the side chain in position 8 is especially β. Preferred compounds are such in which $R_1$=H; $R_2$=$(C_{1-6})$alkyl, $R_3$=H, both $R_4$'s together are oxo, $R_5$=unsubstituted 2-pyrazinyl, n=0, $R_6$ and $R_7$ each are H, and the configuration of the side chain in position 8 is β.

A group of compounds comprises the compounds of formula Ia

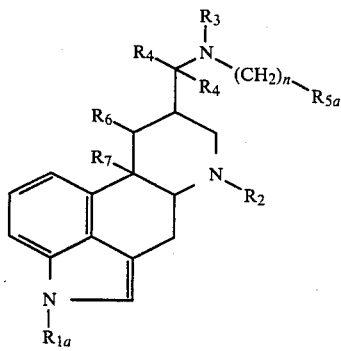

wherein
$R_{1a}$ is H or methyl
$R_2$ is H or $(C_{1-6})$alkyl
$R_3$ is H or $(C_{1-4})$alkyl
the two
$R_4$'s each represent H or together represent an oxo group
$R_{5a}$ is the radical

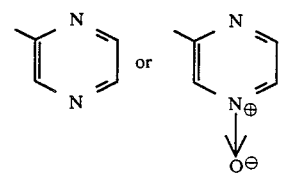

which are unsubstituted or are substituted by 1 or 2 halogen atoms
$R_6$ and $R_7$ both are H or together are a bond and n is 0 or 1.

The present invention in another aspect provides a process for the production of a compound of the invention, which includes the step of
(a) acylating a compound of formula II

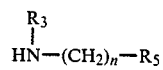

wherein R$_3$, R$_5$ and n are as defined above with a compound of formula III

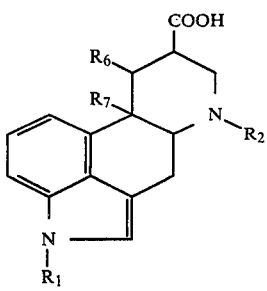

wherein R$_1$, R$_2$, R$_6$ and R$_7$ are as defined above or with a reactive functional acid derivative thereof, to produce a compound of formula I wherein the two R$_4$'s together represent an oxo group,
(b) reducing a compound of formula Ib

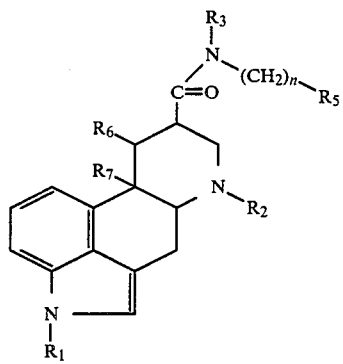

wherein R$_1$ to R$_3$ and R$_5$ to R$_7$ and n are as defined above to produce a compound of formula I wherein the two R$_4$'s each represent H, or
(c) alkylating a compound of formula Ic

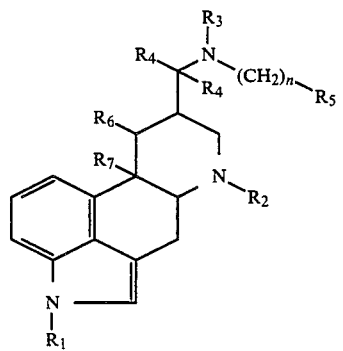

wherein R$_1$ to R$_7$ and n are as defined above with the proviso that at least one of R$_1$ to R$_3$ is hydrogen,
to produce the corresponding compound wherein at least R$_1$ is (C$_{1-4}$)alkyl or an appropriate precursor of H, R$_2$ is (C$_{1-6}$)alkyl and/or R$_3$ is (C$_{1-4}$)alkyl.

In process (a) the starting materials of formula II and III are known—e.g. compounds II from Gazz. Chim. Ital. 91, 1431 (1961) and 93,339 (1963) and from J. Org. Chem. 38,2049 (1973), or they may be produced from known compounds using known methods. Conventional ergoline amide synthesis reactions may be used, preferably using reactive functional acid derivative of a compound of formula III. Thus, the starting materials of formula III may preferably be amidated in known manner by an active ester, e.g. by means of a reaction with oxalyl chloride and dimethylformamide in the presence of pyridine in a suitable solvent e.g. acetonitrile, with a pyrazine of formula II containing an aminogroup e.g. as described in the Swiss Patent Specification No. 588.486.

In process (b) the oxo group in the amides of formula Ib may be reduced by known methods, e.g. in an inert solvent, using a complex metal hydride, e.g. lithium hydride.

In process (c) the alkylation may be effected in conventional manner, using appropriate alkylating agents to alkylate the appropriate group.

The term alkylation includes not only the introduction of an unsubstituted alkyl radical but also the introduction of —CH$_2$OH and (C$_{1-4}$)alkoxymethyl. Where selective alkylation is required, it may be desirable to block temporarily other reactive groups present. Introduction of the CH$_2$OH radical in position 1 may be effected with formaldehyde. The CH$_2$OH radical may be subsequently etherified with an alkanol, e.g. methanol, under acidic conditions.

Introduction of an alkyl group R$_3$ in the side chain may be effected by an alkylation agent in the presence of a base, e.g. sodium hydride, in tetrahydrofuran.

However, instead of introduction an alkyl group R$_3$ as a final reaction step, process (a) is preferred starting from a compound of formula II in which R$_3$ is the appropriate alkyl group.

Introduction of an alkyl group R$_2$ in position 6 may be effected by reductive alkylation, e.g. in case of a methyl group by reaction with formaldehyde and NaBH$_4$, or, generally by an alkyl halide in the presence of a base, e.g. K$_2$CO$_3$.

The compounds of formula I may be recovered in, for example, free base form or acid addition salt form. Mixtures of 8$\alpha$ and 8$\beta$ ergolines may result. These may be separated conventional manner, e.g. by thin layer chromatography or crystallization. The two isomers may be distinguished by conventional spectroscopic means, e.g. n.m.r. spectroscopy as indicated hereinafter in Example 9.

Starting materials if unknown may be prepared in analogous manner to similar known compounds or in analogous manner to that described herein.

The acid addition salt forms of a compound of formula I may be produced in conventional manner from the free base forms and vice versa. Suitable acids include hydrochloric acid, methanesulphonic acid, fumaric acid, tartaric acid or maleic acid.

In the following Examples all temperatures are in degrees centigrade and are uncorrected.

EXAMPLE 1

6-methyl-N-pyrazinylergoline-8$\beta$-carboxamide 850 ml of dimethyl formamide and 700 ml of acetonitrile are placed in a three-necked flask at −20° in a nitrogen atmosphere. A solution of 98 g of oxalyl chloride in 200 ml of acetonitrile is added in drops at the same temperature with vigorous stirring over the course of 25 minutes. The reaction mixture is stirred for a further 15 minutes at −20°, and then 189 g of 6-methylergoline-8$\beta$-carboxylic acid are added. The greyish-green suspension is stirred for one hour at 0°, then a solution of 86.5 g of aminopyrazine in 500 ml of pyridine is added to he reaction mixture which has been cooled to −35°. After stirring for three hours at 0°, the reaction mixture is poured onto 2N soda solution and extracted with methylene chloride. The product which is obtained by evaporating the solvent is purified by crystallisation from ethyl acetate.

M.p.: 223°–224° $[\alpha]_D^{20} = -122.1°$ (c=1.89 in DMF).

hydrochloride (from methanol), m.p.: 225° (decomp.) $[\alpha]_D^{20} = -100.1°$ (c=1.62 in DMF).

hydrogen fumarate (from methanol), m.p.: 245°–248° (decomp.)

L(+)-tartrate (from methanol), m.p.: 215°–225° (decomp.)

methane sulphonate (from methanol), m.p.: 258°–261° (decomp.)

hydrogen maleinate (from methanol), m.p.: 151°–153° (decomp.)

EXAMPLE 2

6-ethyl-N-pyrazinylergoline-8β-carboxamide

In an analogous manner to that described in the foregoing Example, the crude 6-ethyl-N-pyrazinylergoline-8β-carboxamide is prepared from 6-ethylergoline-8β-carboxylic acid (obtainable by ethylation of the corresponding 6-nor compound in accordance with Helv. Chim. Acta, 53, 2197–2201 (1970)) as a starting product. The crude product is purified by chromatography on a column of silica gel. The product, which is obtained using 6% methanol in methylene chloride as the eluant, is crystallised from methylene chloride/n-hexane.

M.p.: 151°–155°, (decomp.)
$[\alpha]_D^{20} = -109.2°$ (c=1.63 in DMF).

EXAMPLE 3

1,6-Dimethyl-N-pyrazinylergoline-8β-carboxamide

In an analogous manner to that described in Example 2, 6-ethyl-N-pyrazinylergoline-8β-carboxamide is prepared from 1,6-dimethylergoline-8β-carboxylic acid (prepared from 6-methylergoline-8β-carboxylic ethylester, in accordance with the process described in Helv. Chim. Acta 40, 1721 (1957)) as a starting compound.

The product is obtained by crystallisation from acetone. Decomposition without melting above 200°.
$[\alpha]_D^{20} = -57.3°$ (c=0.66 in pyridine).

EXAMPLE 4

1-Methoxymethyl-6-methyl-N-pyrazinylergoline-8β-carboxamide 4 g of 6-Methyl-N-pyrazinylergoline-8β-carboxamide (see Example 1) dissolved in 42 ml of acetic acid are placed in a three-necked bottle and diluted with 200 ml of water. 42 ml of an aqueous formaldehyde solution (35% of weight) are added. The mixture is stirred for three hours at 60°–70°, cooled to 20°, adjusted to a pH-value of 8 with a 5N sodium hydroxide solution and extracted with methylene chloride. After evaporation of the solvent, 3.28 g of the obtained crude product, 1-hydroxymethyl-6-methyl-N-pyrazinylergoline-8β-carboxamide, are dissolved in 270 ml of absolute methanol after which 52 g tartaric acid is added and the mixture is stirred for three hours at 60°. The solvent is evaporated in vacuo. The residue is taken up in water, neutralized with a 2N potassiumbicarbonate solution and extracted with methylene chloride. The crude product, obtained after evaporation of the solvent, is purified by chromatography on a column of silica gel. The product is eluted with 3% methanol in methylene chloride and is dissolved in acetone. Two equivalents of tartaric acid are added to form the tartaric acid addition salt.

Decomposition without melting of the crystalline salt above 140°.
$[\alpha]_D^{20} = -57.1°$ (c=0,565 in ethanol).

EXAMPLE 5

6-Methyl-N-(4-oxido-2-pyrazinyl)ergoline-8β-carboxamide

In an analogous manner to that described in Example 1, 6-methyl-N-(4-oxido-2-pyrazinyl)ergoline-8β-carboxamide is prepared from 2-aminopyrazine-4-oxide (prepared according to Gazz. Chim. Ital. 93, 339 (1963)) as a starting compound. After pouring onto a 2N-soda solution and extracting with a mixture of methylene chloride and ethanol (85:15) and evaporating the solvent, the crude product is purified by chromatography on a column of silica gel. The product which is obtained by using 10% methanol in methylene chloride as the eluant, is crystallised from methanol.

Decomposition without melting above 220°.
$[\alpha]_D^{20} = -73.8°$ (c=0.6 in dimethylformamide).

EXAMPLE 6

6,N-Dimethyl-N-pyrazinylergoline-8β-carboxamide

In an analogous manner to that described in Example 1, 6-N-dimethyl-N-pyrazinylergoline-8β-carboxamide is prepared from methylaminopyrazine (obtained according to J. Chem. Soc. (1960) 242) as a starting compound.

After pouring onto a 2N-sodiumbicarbonate solution and extracting with a mixture of methylene chloride and ethanol (9:1) and evaporating the solvent, the crude product is purified by chromatography on a column of silica gel. The product which is obtained by using 9% methanol in methylene chloride as the eluant, is dissolved in ethanol and is treated with an equivalent quantity of 4N hydrochloric acid.

The obtained hydrochloric acid addition salt decomposes without melting above 256°.
$[\alpha]_D^{20} = -54.1°$ (c=1 dimethylformamide).

EXAMPLE 7

6-methyl-N-(2-pyrazinylmethyl)ergoline-8β-carboxamide

In an analogous manner to that described in Example 1, 6-methyl-N-(2-pyrazinylmethyl)ergoline-8β-carboxamide is prepared from aminomethylpyrazine (obtained according to J. Org. Chemistry 38, 2049 (1973)) as a starting compound.

After pouring onto a 2N-soda solution and extracting with methylene chloride and evaporating the solvent, the crude product is purified by chromatography on a column of silica gel using methylene chloride/methanol/concentrated ammonia (93:7:0.7) as the eluant. The pure product is crystallised from ethanol/n-hexane.

Decomposition without melting above 194°.
$[\alpha]_D^{20} = -93.0°$ (c=1,0 in dimethylformamide).

EXAMPLE 8

6-Methyl-N-(1H-2-oxopyrazin-3-yl)ergoline-8β-carboxamide

In an analogous manner to that, described in Example 1, 6-methyl-N-(1H-2-oxopyrazin-3-yl)ergoline-8β-carboxamide is prepared from 3-amino-1H-2-oxopyrazine (obtained according to J. Am. Chem. Soc. 78, 242 (1956)) as a starting compound.

The reaction mixture is poured onto a 2N soda solution, saturated with sodium chloride and filtered.

The residue is purified by chromatography on a column of silica gel. The product, which is obtained by using 20% methanol in methylene chloride as an eluant, is dissolved in methanol and is treated with an equivalent quantity of methane-sulphonic acid. The obtained crystalline methane sulphonate salt decomposes without melting above 220°.

$[\alpha]_D^{20} = -90.6°$ (c=0.5 in dimethylformamide).

EXAMPLE 9

N-(5-Bromopyrazin-2-yl)-6-methylergoline-8β-carboxamide

In an analogous manner to that described in Example 1, N-(5-bromopyrazin-2-yl)-6-methylergoline-8β-carboxamide is prepared from 2-amino-5-bromopyrazine (obtained according to J. Heterocyclic Chemistry 19, 653 (1982)) as a starting compound.

After pouring onto a 2N soda solution and extracting with a mixture of methylene chloride and ethanol (9:1) and evaporating the solvent, the crude product is purified by chromatography on a column of silica gel. The compound is eluted with a mixture of methylene chloride/methanol/concentrated ammonia (97:3:0.3), dissolved in ethanol and treated with an equivalent quantity of 4N hydrochloric acid.

The obtained hydrochloric acid addition salt decomposes without melting above 235°.

$[\alpha]_D^{20} = -74.6°$ (c=1.0 in dimethylformamide).

EXAMPLE 10

6-Methyl-N-pyrazinylergoline-8β-methanamine 400 ml of tetrahydrofuran and 8.73 g of Lithiumaluminiumhydride are placed in a three-necked bottle in a nitrogen atmosphere.

To the suspension, cooled to −5°, a solution of 10 g 6-methyl-N-pyrazinylergoline-8β-carboxamide in 200 ml of tetrahydrofuran is added dropwise.

The green-yellowish suspension is stirred for 3½ hours at 0°, after which 60 ml of water/tetrahydrofuran (1:1) are added.

After stirring for 1½ hours at room temperature the mixture is filtered. The crude product, obtained by evaporation of the filtrate, is purified by chromatography on a column of silica gel.

The product obtained by using 15% methanol in methylene chloride as an eluant is crystallised from methanol.

Decomposition without melting above 245°.

$[\alpha]_D^{20} = -96.9°$ (c=1.0 in dimethylformamide).

EXAMPLE 11

9,10-Didehydro-6-methyl-N-pyrazinylergoline-8α-carboxamide and 9,10-Didehydro-6-methyl-N-pyrazinylergoline-8β-carboxamide 18.8 g 9,10-Didehydro-6-methylergoline-8β-carboxylic acid in 210 ml of acetonitrile are placed in a three-necked bottle at −20° in a nitrogen atmosphere.

A mixture of 8 g trifluoroacetic acid and 14.7 g trifluoroacetic anhydride in 40 ml of acetonitrile is added within 2 minutes at the same temperature.

The brownish reaction mixture is stirred for 15 minutes at −20°.

At the same temperature, a mixture of 4.75 g aminopyrazine in 75 ml pyridine is added.

The mixture is warmed up to 0° within 15 minutes and is stirred for 4½ hours.

The reaction mixture is poured onto 2N soda solution and extracted with methylene chloride. The crude product, obtained after evaporation of the solvent, is purified by chromatography on a column of silica gel.

The foam, which is obtained by using 2% methanol in methylene chloride as an eluant, shows in the proton resonance spectrum a mixture of isomeric 8-carboxamides in a weight proportion 8α:8β=9:1.

In the proton resonance spectrum both components show a distinct position and multiplicity of their vinylic protons in position 9 of the formulae.

In 9,10-didehydro-6-methyl-N-pyrazinyl-ergoline-8α-carboxamide the signal of this proton is a doublet at 6.59 ppm (CDCl$_3$, relatively to tetramethylsilane) with a vicinal coupling constant value of 5.5 Hz under the same conditions. The same proton of the 8β-isomeric component shows a signal of a broad singlet at 6.45 ppm.

In an analogous manner the following compounds of formula I may be prepared:

| Ex. | R$_1$ | R$_2$ | R$_3$ | R$_4$ | R$_4$ | R$_5$ | n | R$_6$ | R$_7$ | Konf. |
|---|---|---|---|---|---|---|---|---|---|---|
| A | n-C$_3$H$_7$ | n-pentyl | n-propyl | H | H | 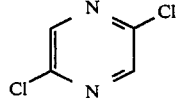 | 1 | H | H | β |
| B | n-C$_3$H$_7$ | n-C$_3$H$_7$ | C$_2$H$_5$ | ‖O | | 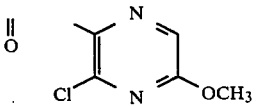 | 2 | bond | | β |
| C | n-C$_3$H$_7$ | n-C$_3$H$_7$ | H | ‖O | | 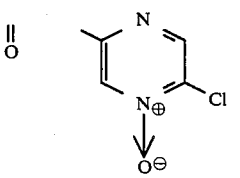 | 2 | H | H | β |

The compounds of the invention are useful because they possess pharmacological activity in animals and are therefore of use as pharmaceuticals.

In particular they have a vasoconstrictor activity which can be demonstrated in vitro on spiral of the canine external carotid artery (E. Müller-Schweinitzer Naunyn-Schmiedebergs Arch. Pharmacol. 292, 113-118, 1976) in concentrations of from $10^{-8}$ to $10^{-5}$ Mol/liter.

Moreover, the compounds of the invention exhibit a dose-dependent reduction of the arteriovenous shunt blood flow in the carotid area of cats and dogs, without significant influence on blood pressure and heart frequency.

In one test the reduction of arteriovenously shunted blood flow is observed in the carotid area in cats under chloralose/urethane anesthesia, measured after administration of the active substance and after injection of microspheres (method described by R. P. Hof et al, in Basic Res. Cardiol. 75, (1980) 747-756) into the carotid artery.

A significant reduction is observed on i.v. administration of 10 to 600 μg/kg animal body weight of the compounds.

In a second test the reduction in arteriovenous shunting is observed by an increase in the arteriovenous $O_2$ saturation difference between the carotid artery and jugular vein in the carotid area in the normotensive anaesthetized dog.

The increase is observed on administration i.v. of from about 20 to about 2000 μg/kg animal body weight of the compounds.

The compounds are therefore useful in the treatment of vascular headaches. Vascular headaches that may be treated include migraine and cluster headaches. The compounds may be administered to treat headaches already present, i.e. acute therapy or to prevent the occurence of headaches, i.e. interval therapy.

For this use the dosage will of course vary depending on the compounds employed, mode of administration and therapy desired. However, in general, satisfactory results are obtained with a daily dosage of from about 0.02 to about 0.2 mg/kg for interval therapy and from about 0.05 to about 0.5 mg/kg sublingually for acute therapy.

Especially for interval therapy the unit dosage may be administered in divided doses e.g. 2-3 times a day.

For the larger mammal the total daily dosage is in the range from about 1 to about 10 mg per os or from about 1 to about 10 mg sublingually for interval therapy, and from about 0.5 to about 5 mg sublingually for acute therapy, admixed with a solid or liquid pharmaceutical carrier or diluent.

An example of a daily dosage for larger mammals is from 1 to 10 mg for the compound of Example 1.

The compounds of the invention may be administered in similar manner to known standards for use for the above indication.

The suitable daily dosage for a particular compound will depend on a number of factors, such as its relative potency of activity and the duration of the activity.

The compound of Example 1 exhibits in the above mentioned test with cats very quickly after sublingual administration, particularly after 30 minutes, the measured activity with a rapid onset and with a duration of at least 2 hours.

The compound of Example 1 is, if administered sublingually, about 10 times more potent than ergotamine after sublingual administration, which means that the compound, if administered sublingually, is active at the same or lower dosages as ergotamine.

The compounds of the invention additionally lead to a selective increase in the tonus of the venous system as indicated in the known Mellander test with cats upon administration of from about 5 to about 45 μg/kg i.v. animal body weight.

On the other hand, the resistant vessels constrict only moderately and for a short time.

The compounds are therefore useful in the treatment of orthostatic hypotension.

For this use the dosage will, of course, vary depending on the compound employed, mode of administration and therapy desired. However, satisfactory results are obtained with a daily dosage of from about 0.05 to about 5 mg/kg animal body weight, conveniently given in divided doses 3 times a day or in sustained release form.

For the larger mammal the total daily dosage is in the range from about 5 to about 20 mg of the compounds, admixed with a solid or liquid pharmaceutical carrier or diluent.

An example of a daily dosage for larger mammals is from 2 to 10 mg for the compound of Example 1.

The compound of Example 1 is particularly interesting.

A compound of formula I may be administered in free base or in pharmaceutically acceptable acid addition salt form. Such salt forms exhibit the same order of activity as the free base forms.

The present invention also provides a pharmaceutical composition comprising a compound of the invention in free base form or in pharmaceutically acceptable acid addition salt form in association with a pharmaceutical carrier or diluent.

Such compositions may be prepared by conventional techniques to be in conventional forms, for example, capsules or tablets.

We claim:

1. A compound of formula I

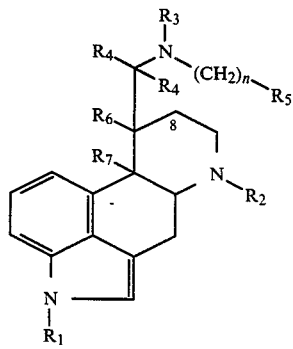

wherein
$R_1$ is H, $(C_{1-4}$alkyl, $-CH_2OH$ or $(C_{1-4})$alkoxymethyl
$R_2$ is H or $(C_{1-6})$alkyl
$R_3$ is H or $(C_{1-4})$alkyl
the two
$R_4$'s both represent H or together represent an oxo-group
$R_5$ is the group or is the group

[pyrazine N-oxide structure]

R₆ and R₇ both represent H or together represent a bond and
n is 0, 1 or 2
in free base form or in pharmaceutically acceptable acid addition salt form.

2. A compound of claim 1 of formula Ia

[Formula Ia structure]

wherein
R₁ₐ is H or methyl
R₂ is H or (C₁₋₆)alkyl
R₃ is H or (C₁₋₄)alkyl
the two
R₄'s each are H or together are an oxo group
R₅ₐ is the group

[two pyrazinyl structures: pyrazinyl or pyrazinyl N-oxide]

R₆ and R₇ both are H or together are a bond and n is 0 or 1
in free base form or in pharmaceutically acceptable acid addition salt form.

3. A compound of formula I of claim 1, which is 6-methyl-N-pyrazinylergoline-8β-methanamine in free base form or in pharmaceutically acceptable acid addition salt form.

4. A compound of claim 1, wherein R₁ is H, (C₁₋₄)alkyl or (C₁₋₄)alkoxymethyl.

5. A compound of claim 1, wherein R₁ is H, methyl or methoxymethyl.

6. A compound of claim 1, wherein R₂ is (C₁₋₄)alkyl.

7. A compound of claim 1, wherein R₂ is methyl or ethyl.

8. A compound of claim 1, wherein R₃ is H or methyl.

9. A compound of claim 1, wherein R₅ is unsubstituted 2-pyrazinyl.

10. A compound of claim 1, wherein R₅ is 4-oxido-2-pyrazinyl.

11. A compound of claim 1, wherein n is 0 or 1.

12. A compound of claim 1, wherein R₆ and R₇ each are H.

13. A compound of claim 1, wherein the configuration of the side chain in position 8 is β.

14. A compound of claim 1 of formula I

[Formula I structure]

wherein
R₁ is H, (C₁₋₄)alkyl, —CH₂OH or (C₁₋₄)alkoxymethyl;
R₂ is H or (C₁₋₆)alkyl;
R₃ is H or (C₁₋₄)alkyl;
the two
R₄'s together represent an oxo-group;
R₅ is the group

[pyrazinyl structure]

or the group

[pyrazinyl N-oxide structure]

R₆ and R₇ both represent H or together represent a bond and
n is 0, 1 or 2,
in free base form or in pharmaceutically acceptable acid addition salt form.

15. A compound of formula I of claim 14, which is 6-methyl-N-pyrazinylergoline-8β-carboxamide in free base form or in pharmaceutically acceptable acid addition salt form.

16. A compound of formula I of claim 14, which is 6-ethyl-N-pyrazinylergoline-8β-carboxamide in free base form or in pharmaceutically acceptable acid addition salt form.

17. A compound of formula I of claim 14, which is 1,6-dimethyl-N-pyrazinylergoline-8β-carboxamide in free base form or in pharmaceutically acceptable acid addition salt form.

18. A compound of formula I of claim 14, which is 1-methoxymethyl-6-methyl-N-pyrazinylergoline-8β-carboxamide in free base form or in pharmaceutically acceptable acid addition salt form.

19. A compound of formula I of claim 14, which is 6-methyl-N-(4-oxido-2-pyrazinyl)ergoline-8β-carboxamide in free base form or in pharmaceutically acceptable acid addition salt form.

20. A compound of formula I of claim 14, which is 6,N-dimethyl-N-pyrazinylergoline-8β-carboxamide in free base form or in pharmaceutically acceptable acid addition salt form.

21. A compound of formula I of claim 14, which is 6-methyl-N-(2-pyrazinylmethyl)ergoline-8β-carboxamide in free base form or in pharmaceutically acceptable acid addition salt form.

22. A compound of formula I of claim 14, which is 9,10-didehydro-6-methyl-N-pyrazinylergoline-8β-carboxamide in free base form or in pharmaceutically acceptable acid addition salt form.

23. A compound of formula I of claim 14, which is 9,10-didehydro-6-methyl-N-pyrazinylergoline-8β-carboxamide in free base form or in pharmaceutically acceptable acid addition salt form.

24. A compound of claim 14, wherein $R_1$ is H, $R_2$ is $(C_{1-6})$alkyl, $R_3$ is H, both $R_4$'s together are oxo, $R_5$ is unsubstituted 2-pyrazinyl, n is 0, $R_6$ and $R_7$ each are H and the configuration of the side chain in position 8 is β.

25. A pharmaceutical composition useful in treating migraine or orthostatic hypotension which comprises a therapeutically effective amount of a compound of claim 1 in association with a pharmaceutical carrier or diluent.

26. A method of treating migraine or orthostatic hypotension which comprises administering a therapeutically effective amount of a compound of claim 1 to a subject in need of such treatment.

* * * * *